(12) United States Patent
Zanella et al.

(10) Patent No.: US 9,861,697 B2
(45) Date of Patent: *Jan. 9, 2018

(54) PHARMACEUTICAL GELS AND METHODS FOR DELIVERING THERAPEUTIC AGENTS TO A SITE BENEATH THE SKIN

(71) Applicant: Warsaw Orthopedic, Inc., Warsaw, IN (US)

(72) Inventors: John M. Zanella, Cordova, TN (US); William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/144,129

(22) Filed: May 2, 2016

(65) Prior Publication Data

US 2016/0243239 A1 Aug. 25, 2016

Related U.S. Application Data

(60) Division of application No. 14/478,382, filed on Sep. 5, 2014, now Pat. No. 9,327,030, which is a continuation of application No. 12/056,511, filed on Mar. 27, 2008, now Pat. No. 8,828,354.

(51) Int. Cl.

| | | |
|---|---|---|
| *A61K 47/10* | (2017.01) | |
| *A61K 9/14* | (2006.01) | |
| *A61K 9/50* | (2006.01) | |
| *A61K 31/573* | (2006.01) | |
| *A61K 38/18* | (2006.01) | |
| *A61K 51/12* | (2006.01) | |
| *C07K 16/24* | (2006.01) | |
| *A61K 9/00* | (2006.01) | |
| *A61K 9/06* | (2006.01) | |

(52) U.S. Cl.
CPC .......... *A61K 47/10* (2013.01); *A61K 9/0024* (2013.01); *A61K 9/06* (2013.01); *A61K 9/14* (2013.01); *A61K 9/50* (2013.01); *A61K 31/573* (2013.01); *A61K 38/1875* (2013.01); *A61K 51/1213* (2013.01); *C07K 16/241* (2013.01); *A61K 9/0019* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 5,514,379 A * | 5/1996 | Weissleder | A61K 9/1658 424/426 |
| 5,879,713 A | 3/1999 | Roth et al. | |
| 6,069,129 A | 5/2000 | Sandberg et al. | |
| 6,179,862 B1 | 1/2001 | Sawhney | |
| 6,287,688 B1 | 9/2001 | Howell et al. | |
| 6,331,311 B1 | 12/2001 | Brodbeck et al. | |
| 6,428,804 B1 | 8/2002 | Suzuki et al. | |
| 6,461,631 B1 | 10/2002 | Dunn et al. | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,773,714 B2 | 8/2004 | Dunn et al. | |
| 2002/0009454 A1 | 1/2002 | Boone et al. | |
| 2002/0090398 A1 | 7/2002 | Dunn et al. | |
| 2004/0018228 A1 | 1/2004 | Fischell et al. | |
| 2004/0018828 A1* | 1/2004 | Adler | H04M 15/00 455/405 |
| 2004/0072799 A1 | 4/2004 | Li et al. | |
| 2004/0082540 A1 | 4/2004 | Hermida Ochoa | |
| 2004/0214793 A1 | 10/2004 | Hermida Ochoa | |
| 2005/0152949 A1 | 7/2005 | Hotchkiss et al. | |
| 2005/0186261 A1 | 8/2005 | Avelar et al. | |
| 2005/0197293 A1 | 9/2005 | Mellis et al. | |
| 2006/0093673 A1 | 5/2006 | Coury et al. | |
| 2006/0148903 A1 | 7/2006 | Burch et al. | |
| 2006/0188583 A1* | 8/2006 | Lim | A61K 9/0024 424/490 |
| 2006/0189944 A1 | 8/2006 | Campbell et al. | |
| 2007/0156180 A1 | 7/2007 | Jaax et al. | |
| 2007/0196415 A1 | 8/2007 | Chen et al. | |
| 2007/0202074 A1 | 8/2007 | Shalaby | |
| 2007/0243225 A1 | 10/2007 | McKay | |
| 2007/0243228 A1 | 10/2007 | McKay | |
| 2008/0091207 A1 | 4/2008 | Truckai et al. | |

FOREIGN PATENT DOCUMENTS

WO   WO03005961 A2   1/2003

OTHER PUBLICATIONS

Cleveland Clinic, Non-Steroidal anti-inflammatory medicines, (http://my.clevelandclinic.org/health/drugs_devices_supplements/hic_Non-Steroidal_Anti-Inflammatory_Medicines_NSAIDs), Dec. 31, 1995.*
Widmark, JM, Imaging related medicationsProc (Bayl Univ Med Cent) 2007; 20 (4): 408-417).*
International Search Report for US Application No. PCT/US2009/036482 dated Oct. 20, 2009.
QLT, Inc., Atrigel Drug Delivery Platform, Jul. 2006.

* cited by examiner

*Primary Examiner* — Celeste A Roney (57) ABSTRACT

Pharmaceutical gels and methods for delivering a therapeutic agent to a target tissue site beneath the skin of a patient are provided, the gel being capable of adhering to the target tissue site and comprising one or more biodegradable depots containing an effective amount of the therapeutic agent. In various embodiments, the gel is sprayable and hardens after contacting the target tissue site.

8 Claims, 3 Drawing Sheets

PHARMACEUTICAL GELS AND METHODS FOR DELIVERING THERAPEUTIC AGENTS TO A SITE BENEATH THE SKIN

This application is a divisional application of U.S. patent application Ser. No. 14/478,382 filed on Sep. 5, 2014, entitled "PHARMACEUTICAL GELS AND METHODS FOR DELIVERING THERAPEUTIC AGENTS TO A SITE BENEATH THE SKIN", which is a continuation of U.S. patent application Ser. No. 12/056,511 filed on Mar. 27, 2008, now U.S. Pat. No. 8,828,354, entitled "PHARMACEUTICAL GELS AND METHODS FOR DELIVERING THERAPEUTIC AGENTS TO A SITE BENEATH THE SKIN". These entire disclosures are incorporated herein by reference into the present disclosure.

BACKGROUND

Localized delivery (e.g., intrathecally, intraspinally, intraarticularly, etc.) of therapeutic agents has become increasingly more popular over the years because it has several advantages over more conventional routes of drug delivery such as oral delivery. Localized delivery has the advantage of allowing the therapeutic agent to be implanted directly at the site where drug action is needed. This becomes especially important for drugs that have unwanted systemic side effects.

Localized delivery of therapeutic agents has the advantage of protecting the therapeutic agent from breakdown due to harsh physiological environments (e.g., gastric and liver enzymes) and thus improves the drug's stability in vivo. This particular feature makes this technology particularly attractive for the delivery of labile drugs such as proteins and peptides. Localized delivery also improves patient compliance. For example, therapeutic agents can be encapsulated and delivered locally allowing the drug to be released over extended periods (e.g., 6 months or longer) and hence eliminates the need for multiple injections. This feature can improve patient compliance especially for drugs for chronic indications, requiring frequent injections.

In the past, localized repeat delivery of therapeutic agents has been used to treat chronic debilitating diseases such as osteoarthritis. Osteoarthritis is a chronic condition that affects millions of people in the world, and it is a type of arthritis that is caused by the chronic breakdown and eventual loss of cartilage in one or more joints. Osteoarthritis often affects synovial joints, such as the knees, hips, fingers, thumbs, neck, and spine. Severe forms of the disease are extremely disabling and restrict a patient's lifestyle. Localized delivery via intraarticular injection of corticosteroids, hyaluronan or hylan provide some short term relief in controlling the pain symptoms of osteoarthritis.

Sciatica, another debilitating disease, can be a painful condition associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area. In the past, localized delivery of corticosteroids (e.g., epidural) has been used to provide short term relief of the inflammation and pain associated with sciatica.

Newer methods are currently being investigated for treatment of chronic debilitating diseases utilizing localized delivery of drug depots. In these treatments typically the drug depot is delivered locally to the treatment site and the drug is released from the depot in a relatively uniform dose over weeks, months or even years. Localized delivery of drug depots is becoming especially important and popular in modulating the immune, inflammation and/or pain responses in treatment of chronic diseases.

Sometimes after the drug depot is implanted at the treatment site, unfortunately, the drug depot may migrate from the implant site as physiological conditions change (e.g., repair and regeneration of cells, tissue in growth, movement at implant site, etc.). At times, this may reduce efficacy of the drug as the drug depot migrates away from the implant site and lodges in a distant site. If this occurs, often the drug depot will have to be removed from the distant site and be reinserted causing additional physical and psychological trauma to a patient. In some cases, if the drug depot migrates into a joint, the drug depot may inhibit movement. In more severe cases, if the drug depot migrates in a blood vessel, it may restrict blood flow causing an ischemic event (e.g., embolism, necrosis, infarction, etc.), which could be detrimental to the patient.

New drug depot compositions and methods are needed, which can easily allow accurate and precise placement of a drug depot with minimal physical and psychological trauma to a patient. When implanting several drug depots at a time, drug depot compositions and methods are needed that accurately and precisely allow placement of the drug depot in a manner that optimizes location, accurate spacing, and drug distribution.

SUMMARY

New drug depot compositions and methods are provided, which can easily allow accurate and precise implantation of a drug depot with minimal physical and psychological trauma to a patient. One advantage of the drug depot compositions and methods is that the drug depot can now be easily delivered and adheres to the target tissue site (e.g., synovial joint, at or near the spinal column, etc.) using a gel that hardens upon contact with the target tissue. In this way, accurate and precise implantation of a drug depot in a minimally invasive procedure can be accomplished. Another advantage, in various embodiments, is that by utilizing the gel, implantation of the drug depot can now be accomplished without the need to suture the drug depot to the target site reducing physical and psychological trauma to the patient. In various embodiments, the gel is sprayable (utilizes "spray-a-dose" technology) and allows voids in, for example, bones to be filled in so that the drug depot can be delivered directly to the target tissue site. In various embodiments, when several drug depots are to be implanted, the gel allows accurate placement of the drug depot in a manner to optimize location, accurate spacing, and drug distribution.

In one exemplary embodiment, a gel for delivering a therapeutic agent to a target tissue site beneath the skin of a patient is provided, the gel being capable of adhering to the target tissue site and comprising one or more biodegradable depots containing an effective amount of the therapeutic agent, wherein the target tissue site comprises at least one muscle, ligament, tendon, cartilage, spinal disc, spinal foraminal space near the spinal nerve root, facet or synovial joint, or spinal canal.

In another exemplary embodiment, a method is provided for delivering a therapeutic agent into a synovial joint of a patient, the method comprising inserting a cannula or needle at or near a target tissue site in the synovial joint and spraying a gel capable of adhering to the target tissue site in the synovial joint, the gel comprising one or more biodegradable depots containing an effective amount of the therapeutic agent.

In yet another exemplary embodiment, a method for delivering a therapeutic agent into a target tissue site beneath the skin is provided, the method comprising inserting a cannula or needle at or near a target tissue site and injecting a gel capable of adhering to the target tissue site, the gel comprising one or more biodegradable depots containing an effective amount of the therapeutic agent, wherein the target tissue site comprises a spinal disc, spinal foraminal space near the spinal nerve root, facet joint, spinal canal, or bone.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug depot compositions and methods are provided, which can easily allow accurate and precise implantation of a drug depot with minimal physical and psychological trauma to the patient. The drug depot compositions and methods provided utilize a gel that adheres to the target tissue site (e.g., synovial joint, at or near the spinal column, etc.), and in various embodiments, hardens on contact with the target tissue site. In this way, accurate and precise implantation of a drug depot in a minimally invasive procedure can be accomplished. In various embodiments, the gel avoids the need to suture the drug depot to the target site reducing physical and psychological trauma to the patient. In various embodiments, when several drug depots are to be implanted, the gel allows accurate placement of the drug depot in a manner to optimize location, accurate spacing, and drug distribution. In various embodiments, the drug depot compositions and methods utilize spray-a-dose technology that allows voids in, for example, bones to be filled in so that the drug depot can be delivered directly to the target tissue site.

Drug Depot

In various embodiments, the gel comprises a drug depot. A drug depot comprises a physical structure to facilitate sustained release of the drug in a desired site (e.g., a synovial joint, a disc space, a spinal canal, a tissue of the patient, etc.). The drug depot also comprises the drug. The term "drug" as used herein is generally meant to refer to any substance that alters the physiology of a patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot provides a concentration gradient of the therapeutic agent around the depot for delivery to the site. In various embodiments, the drug depot provides an optimal drug concentration gradient of the therapeutic agent at a distance of up to about 1 cm to about 5 cm from the implant site.

A "therapeutically effective amount" or "effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

Examples of therapeutic agents include, those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basiliximnab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α, interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dilhiocarbamate, and other compounds, such as, for example, sulfasalazine.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

The depot may contain a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The depot comprises the therapeutic agent or agents and may also contain other non-active ingredients. It has a multi-functional purpose including the carrying, stabilizing and controlling the release of the therapeutic agent(s). The controlled release process, for example, may be by a solution-diffusion mechanism or it may be governed by an erosion-controlled process. Typically, the depot will be a solid or semi-solid formulation comprised of a biocompatible material, which can be biodegradable. The term "solid" is intended to mean a rigid material, while, "semi-solid" is intended to mean a material that has some degree of flexibility, thereby allowing the depot to bend and conform to the surrounding tissue requirements.

In various embodiments, the depot material will be durable within the tissue site for a period of time equal to (for biodegradable components) or greater than (for non-biodegradable components) the planned period of drug delivery. For example, the depot material may have a melting point or glass transition temperature close to or higher than body temperature, but lower then the decomposition or degradation temperature of the therapeutic agent. However, the pre-determined erosion of the depot material can also be used to provide for slow release of the loaded therapeutic agent(s).

In various embodiments, the depot may have a high drug loading, such that the therapeutic agent comprises about 0.5-99 wt % of the depot, 1.0-40 wt % of the depot, 5-20 wt % of the depot, or 30-95 wt % of the depot, or 50-95 wt % of the depot. The balance is depot material, including optional inactive materials.

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As function of the chemistry of the biodegradable material the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

A "depot" includes but is not limited to capsules, microspheres, microparticles, microcapsules, microfibers particles, nanospheres, nanoparticles, coating, matrices, wafers, pills, pellets, emulsions, liposomes, micelles, or other pharmaceutical delivery compositions. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot and/or gel will degrade over time by the action of enzymes, by hydrolytic action and/or by other similar mechanisms in the human body. In various embodiments, "biodegradable" includes that the gel and/or depot (e.g., microparticle, microsphere, etc.) can break down or degrade within the body to non-toxic components after or while a therapeutic agent has been or is being released. By "bioerodible" it is meant that the depot and/or gel will erode or degrade over time due, at least in part, to contact with substances found in the surrounding tissue, fluids or by cellular action. By "bioabsorbable" it is meant that the depot and/or gel will be broken down and absorbed within the human body, for example, by a cell or tissue. "Biocompatible" means that neither the depot and/or gel will cause substantial tissue irritation or necrosis at the target tissue site.

In various embodiments, the depot may comprise a bioabsorbable, a bioabsorbable, and/or a biodegradable biopolymer that may provide immediate release, sustained release or controlled release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area or joint area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet, and the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 5.0 mm, such as, for example, from 0.05 to 0.75 mm.

Radiographic markers can be included on the drug depot or gel to permit the user to accurately position the depot or gel into the target site of the patient. These radiographic markers will also permit the user to track movement and degradation of the depot at the site over time. In this embodiment, the user may accurately position the depot or gel in the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles. In various embodiments, the radiographic marker could be a spherical shape or a ring around the depot.

Gel

In one exemplary embodiment, a gel for delivering a therapeutic agent to a target tissue site beneath the skin of a patient is provided, the gel being capable of adhering to the target tissue site and comprising one or more biodegradable depots containing an effective amount of the therapeutic agent, wherein the target tissue site comprises at least one muscle, ligament, tendon, cartilage, spinal disc, spinal foraminal space near the spinal nerve root, facet or synovial joint, or spinal canal.

In various embodiments, the gel includes a substance having a gelatinous, jelly-like, or colloidal properties at room temperature. The gel, in various embodiments, may have the therapeutic agent dispersed throughout it or one or more drug depots comprising the therapeutic agent may be suspended within the gel. The dispersal of the therapeutic agent may be even throughout the gel. Alternatively, the concentration of the therapeutic agent may vary throughout it. As the biodegradable material of the gel or drug depot degrades at the site, the therapeutic agent is released.

In another exemplary embodiment, the gel in viscous form is loaded with one or more drug depots (e.g., microspheres loaded with a therapeutic agent), wherein the viscous gel is positioned into a synovial joint, disc space, a spinal canal, or a soft tissue surrounding the spinal canal of a subject. The gel can also be used, in various embodiments, to seal or repair tissue. In yet another exemplary embodiment, the gel is a sprayable, injectable, and/or an adherent gel that solidifies upon contact with tissue. For example, the gel may be administered as a liquid that gels in situ at the target tissue site. In various embodiments, the gel can comprise a two part system where a liquid is administered and a gelling agent is added subsequently to cause the liquid to gel or harden.

In various embodiments, the gel is a hardening gel, which is separate from the drug depot and applied before, during or after implantation of the drug depot. After the gel is applied to the target site, it hardens holding the drug depot in place in this way the need to suture the depot to the target tissue site is avoided.

In various embodiments, the viscous gel is loaded with a drug depot, which delivers the therapeutic agent to the desired target tissue site (e.g., inflamed tissue, degenerative tissue, etc.) and prevents the drug depot from being removed from that site by the venous systemic circulation or otherwise dispersed too widely, which reduces the desired therapeutic effect. For example, after hours or days, the gel may be absorbed, thereby allowing the drug depots (e.g., microspheres) to begin releasing the therapeutic agent. The microspheres may not begin releasing the agent until they are released from the gel. So, the microspheres may be formed from an insoluble or inert substances, but soluble or active once it comes into contact with the target tissue site. Likewise, the gel may comprise a substance that dissolves or disperses within the tissue. As the gel begins to dissolve within hours to days, the drug depots (e.g., microspheres) are exposed to body fluids and begin releasing their contents. So, the gel may comprise the same or different material as the drug depot (e.g., POE, PEG). The gel and drug depot can be formulated to optimize exposure time of the drug depot and release of the therapeutic agent from the drug depot.

In various embodiments, the gel is flowable and can be injected, sprayed, instilled, and/or dispensed to, on or in the target tissue site. "Flowable" means that the gel formulation is easy to manipulate and may be brushed, sprayed, dripped, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the gel may be used to fill one or more voids in an osteolytic lesion.

In various embodiments, the gel comprises poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly(d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the gel in a controlled and/or sustained manner. For example, the gel containing the therapeutic agent and a polymer matrix can be injected at the target tissue site and the polymer matrix breaks down over time (e.g., days, months) within the target tissue site releasing the therapeutic agent. Thus the administration of the gel can be localized and occur over a period of time (e.g., at least one day to about 3, 6, 9 or 12 months).

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the gel and/or drug depot, or a matrix or component thereof, or as the result of metabolic transformation or dissolution of the therapeutic agent(s) or conjugates of therapeutic agent(s).

In various embodiments, the gel and/or drug depot can be designed to cause an initial burst dose of therapeutic agent within the first 24 hours after implantation. "Initial burst" or "burst effect" or "bolus dose" refers to the release of therapeutic agent from the gel and/or depot during the first 24 hours after the gel comes in contact with an aqueous fluid (e.g., synovial fluid, cerebral spinal fluid, etc.). The "burst effect" could be due to the increased release of therapeutic agent from the gel while it is coagulating or hardening to form a solid or semi solid (rubbery) implant, while the gel is still in a flowable state, because of its relatively fast degradation properties, or relatively fast drug diffusion through the gel. In alternative embodiments, the gel and/or depot is designed to avoid this initial burst effect.

In various embodiments, the gel has a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, a depot comprises an adherent gel comprising a therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject or spray the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or adhere to the target tissue. In various embodiments, the gel may also adhere to the targeted tissue site by a mechanical interdigitation with the target tissue prior to hardening. In other embodiments, the gel may adhere to the target tissue site by chemical bonding of the gel to the target tissue site (e.g., ionic bonding, covalent bonding, hydrogen bonding, electrostatic interaction, hydrophobic, hydrophilic or other interaction with target tissue site). In still other embodiments, the gel may adhere to the target tissue site by a combination of chemical bonding and mechanical interdigitation.

In various embodiments, a gel is provided that hardens or stiffens after delivery. Typically, hardening gel formulations may have a pre-dosed modulus of elasticity in the range of about $1 \times 10^4$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times 10^4$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example when applying the formulation via spray.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

When the gel is designed to be a flowable gel, it can vary from low viscosity, similar to that of water, to a high viscosity, similar to that of a paste, depending on the molecular weight and concentration of the polymer used in the gel. The viscosity of the gel can be varied such that the polymeric composition can be applied to a patient's tissues by any convenient technique, for example, by brushing, spraying, dripping, injecting, or painting. Different viscosities of the gel will depend on the technique used to apply the composition. For example, spraying requires a gel composition having a low viscosity.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxyethylmethacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

The sprayability of the gel can also be controlled, among other things, by controlling the particle size distribution of the gel components. In various embodiments, the particle size distribution of the depots suspended in the gel may be in the range of from about 10 µm to 100 µm so that the gel can easily be sprayed at or near the target site.

In contrast, to a sprayable gel that typically employs a low viscosity polymer, a gel with a higher viscosity may be desirable for other applications, for example, a gel having a putty-like consistency may be more preferable for bone regeneration applications. In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres loaded with the therapeutic agent. In one embodiment, the microspheres provide for a sustained release of the therapeutic agent. In yet another embodiment, the gel, which is biodegradable, prevents the microspheres from releasing the therapeutic agent; the microspheres thus do not release the therapeutic agent until they have been released from the gel. For example, a gel may be deployed around a target tissue site (e.g., a nerve root). Dispersed within the gel are a plurality of microspheres that encapsulate the desired therapeutic agent. Certain of these microspheres degrade once released from the gel, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site. The present invention also contemplates the use of adherent gels to so constrain dispersal of the therapeutic agent. These gels may be deployed, for example, in a disc space, in a spinal canal, or in surrounding tissue, or in a joint space, such as a synovial cavity. In this embodiment the gel is an adherent and/or settable gel in order to stay in place within a joint space.

Cannula or Needle

It will be appreciated by those with skill in the art that the gel can be administered to the target site using a cannula or needle that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, gel, and/or medical device to administer the drug may be sterilizable. In various embodiments, one or more components of the drug depot, gel, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the gel, depot and/or one or more components of the device, including, but not limited to, gas sterilization, such as, for example, with ethylene oxide or steam sterilization.

In various embodiments, a kit is provided which may include additional parts along with the gel and/or drug depot, medical device combined together to be used to implant the gel and/or drug depot. The kit may include the drug depot device in a first compartment. The second compartment may include a canister holding the gel and/or drug depot to be sprayed at the target site, and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

Drug Delivery

In various embodiments, a method for delivering a therapeutic agent into a synovial joint of a patient is provided, the method comprising inserting a cannula at or near a target tissue site in the synovial joint and implanting the drug depot at the target site beneath the skin of the patient and brushing, spraying, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered (e.g., brushed, sprayed, dripped, injected, or painted, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, sprayed, dripped, injected, or painted, etc.) around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a joint or spinal region, a portion of fluid (e.g., synovial fluid, spinal fluid, etc.) can be withdrawn from the target site through the cannula or needle first and then the gel administered (e.g., brushed, sprayed, dripped, injected, or painted, etc.). The target site will re-hydrate (e.g., replenishment of fluid) and this aqueous environment will cause the drug to be released from the depot or the gel.

The gel may be used for localized delivery of the therapeutic agent to the patient to treat a disease or condition such as for example, osteoarthritis, rheumatoid arthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like. In various embodiments, the gel may also be used to repair tissue as well deliver a therapeutic agent.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots, gels or depot dispersed in the gel having a quantity of therapeutic agent that can be deposited at or near the target site as needed for treatment of pain, inflammation or other disease or condition.

In various embodiments, the gel may be used to treat rheumatoid arthritis (RA) and/or osteoarthritis by inserting a cannula at or near a target tissue site and implanting the drug depot at the target site beneath the skin of the patient and brushing, spraying, dripping, injecting, or painting the gel at the target site to hold or have the drug depot adhere to the target site. In this way unwanted migration of the drug depot away from the target site is reduced or eliminated.

RA is a chronic systemic disease characterized by progressive joint deformity and joint destruction in which cytokines play a central pathogenic role. The clinical course of RA is variable and often shows a remitting pattern. Three forms of RA can be distinguished: mild, self-limiting disease; mildly progressive disease; and aggressive disease, which is difficult to control with medication, and is characterized by functional decline and radiologic deterioration of the joints, e.g., joint space narrowing and erosions. In accordance with the systemic nature of RA, there are extra-articular manifestations, which include vasculitis, alveolitis, and ocular disease. Onset of RA is often insidious with fatigue, anorexia, generalized weakness, and vague musculoskeletal symptoms. Specific symptoms appear later. Several joints, usually in a symmetrical fashion, are affected. Most often these are joints of the hands, wrists, knees, and feet. Joints are painful and swollen, and motion is limited. With persistent inflammation, a variety of deformities develop which include most typically radial deviation of the wrist and hyperextension or flexion of the proximal interphalangeal joints; other deformities occur as well. Atrophy of skeletal muscle sets in. In approximately 20 to 30% of all patients, there is development of rheumatoid nodules on periarticular structures or sites of trauma, but they are usually of limited clinical significance. The nodules may be found in other structures such as the pleura or the meninges. Laboratory findings may include elevation of erythrocyte sedimentation rate (ESR) and C-reactive protein (CRP) along with rheumatoid factor. Rheumatoid factor is an autoantibody against the Fc portion of IgG found in more than two-thirds of all patients. High titers of rheumatoid factor are a good indicator of disease activity. Mild anemia (normochromic, normocytic) and eosinophilia may be present as well. With progression of the disease, X-ray abnormalities such as general deformity, juxta-articular osteopenia, loss of articular cartilage, and bone erosion become more evident.

In one exemplary embodiment, the gel is utilized to treat osteoarthritis (OA), which is the most common form of arthritis in Western populations. Knee OA, characterized clinically by pain and functional disability, is the leading cause of chronic disability among the elderly in the US. Risk factors for OA include age, gender, race, trauma, repetitive stress/joint overload, muscle weakness, and genetic factors. Pathologically, the most striking changes in OA are focal loss of articular cartilage and marginal and central new bone formation. However, OA is not simply a disease of articular cartilage and the subchondral bone. Rather, it is a disease of the synovial joint, with alterations also found in the synovium, capsule, ligaments, periarticular muscle, and sensory nerves.

Although OA was once considered a non-inflammatory arthropathy, patients often present with signs and symptoms consistent with local inflammation and synovitis, and inflammation and inflammatory mediators play a role in the joint destruction associated with OA as well as in pain. Both chondrocytes and synovium in OA can produce proinflammatory cytokines, including IL-1β, which can alter cartilage homeostasis in favor of cartilage degradation. For example, IL-1β appears to be a major factor stimulating matrix metalloproteinase synthesis and other cartilage catabolic responses in OA.

Figure 1:
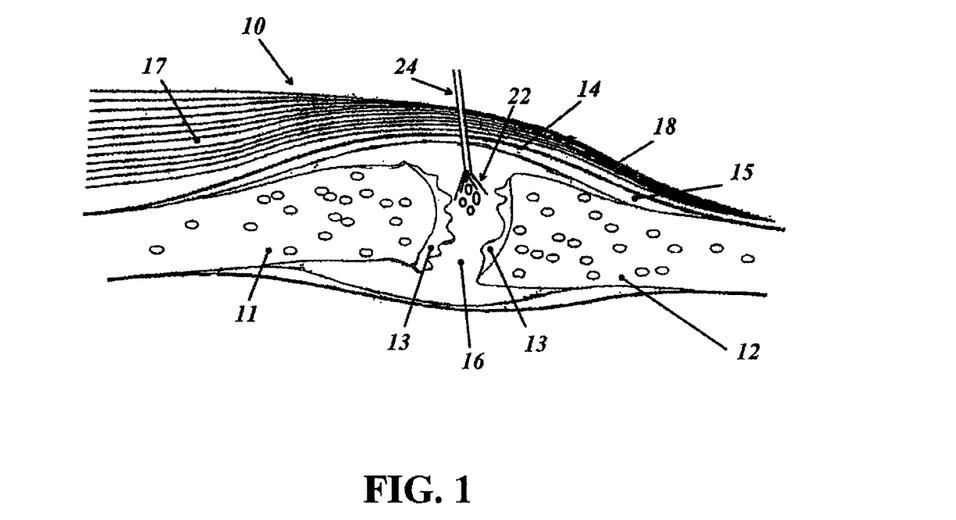
FIG. 1 illustrates a side sectional view of a joint affected by osteoarthritis and delivery of an embodiment of a sprayable gel containing a plurality of drug depots inserted into the synovial joint via a cannula or needle.

FIG. 1 illustrates one embodiment of the effect of osteoarthritis on the joint 10. Osteoarthritis causes the cartilage 13 to become worn away from the ends of the bones 11, 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11, 12 stable and allow the joint 10 to bend and move. However, symptoms become worse and debilitating as the disease progresses. To treat the diseased joint, the gel 22 can be administered locally at the target site utilizing a cannula or needle 24 that penetrates beneath the skin to the target site 22. In this embodiment, the gel contains the depot suspended in it and the gel is sprayed at the target site (shown at or near the osteolytic lesions). It will be understood that some synovial fluid 16 may be withdrawn from the joint 10 and the gel added before, during, or after the synovial fluid is withdrawn so that as the joint rehydrates, the therapeutic agent will be released as the fluid contacts the drug depot. The gel may also be placed at other target sites (e.g., by the meniscus or cartilage surface) and the drug released. In this way, accurate and precise implantation of a drug depot in a minimally invasive procedure can be accomplished. In various embodiments, the gel avoids the need to suture the drug depot to the target site reducing physical and psychological trauma to the patient. In various embodiments, when several drug depots are to be implanted, the gel allows accurate placement of the drug depot in a manner to optimize location, accurate spacing, and drug distribution.

Figure 2:
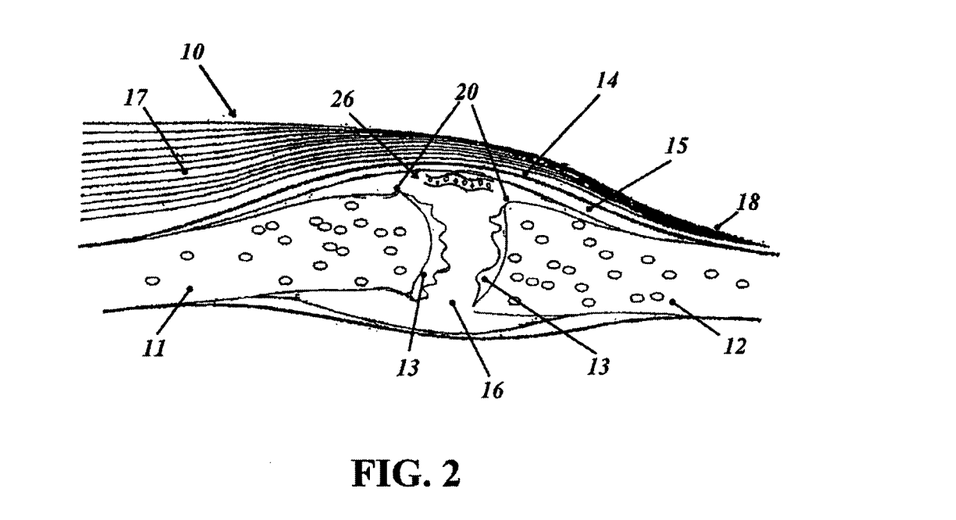
FIG. 2 illustrates a side sectional view of a joint affected by osteoarthritis and delivery of an embodiment of a gel containing a plurality of drug depots, which adheres and hardens after contact with the target tissue, in this case, a synovial joint.

FIG. 2 illustrates one embodiment of the effect of osteoarthritis on the joint 10. Osteoarthritis causes the cartilage 13 to become worn away from the ends of the bones 11 and 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11 and 12 stable and allow the joint 10 to bend and move. However, symptoms become worse and debilitating as the disease progresses. To treat the diseased joint, the gel can be administered locally at the target site utilizing a cannula or needle that penetrates beneath the skin to the target site. In this embodiment, the gel comprises the depot suspended in the gel and the gel is sprayed near the target site (shown near the osteolytic lesions). In this embodiment, the gel has adhering and hardening characteristics 26 and adheres and hardens in an area that does not interfere with movement of the joint and is away from the articular surfaces of the joint. As the synovial fluid contacts the hardening gel, the therapeutic agent suspended therein is released.

Figure 3:
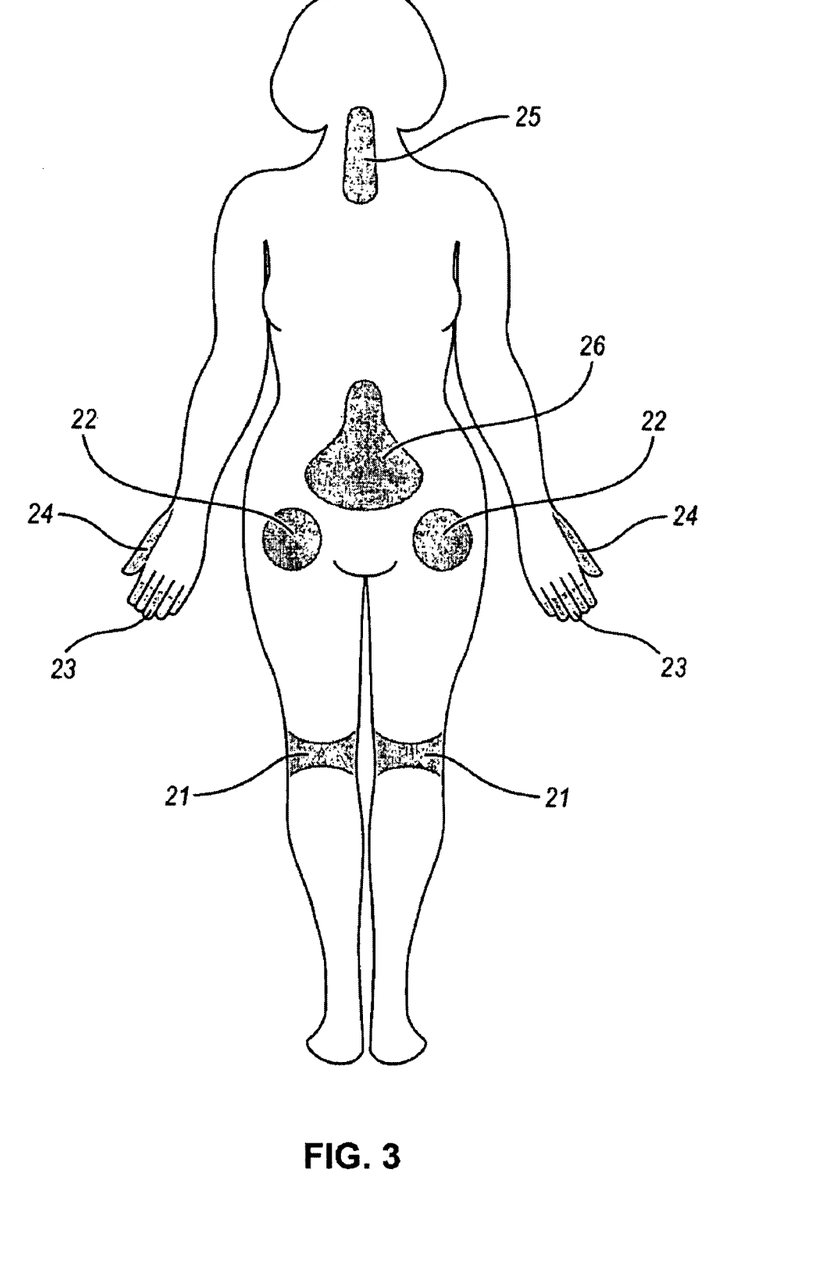
FIG. 3 illustrates a number of common locations within a patient that may be affected by osteoarthritis and locations that the pharmaceutical gel can locally be administered thereto and used to fill voids in bone.

FIG. 3 illustrates a number of common locations within a patient that may be affected by osteoarthritis. It will be recognized that the locations illustrated in FIG. 3 are merely exemplary of the many different locations within a patient that may be affected by osteoarthritis. For example, osteoarthritis may affect a patient's knees 21, hips 22, fingers 23, thumbs 24, neck 25, and spine 26. Osteoarthritis in the hips 22 can cause pain, stiffness, and severe disability. Patients may feel the pain in their hips 22, groin, inner thigh, buttocks, or knees.

Osteoarthritis in the fingers 23 may cause the fingers 23 to become enlarged and gnarled. The disease may cause small, bony knobs to appear on the end joints of the fingers 23. These knobs are referred to as Heberden's nodes. Similar knobs, called Bouchard's nodes, can appear on the middle joints of the fingers 23. Affected fingers 23 may ache or be stiff and numb. More women than men suffer from osteoarthritis in the fingers 23, and they develop it especially after menopause. The base of the thumb joint 24 may also be similarly affected by osteoarthritis.

Osteoarthritis in the neck 25 and spine 26 may cause stiffness and pain in the neck or in the lower back. It may also cause weakness or numbness of the arms or legs. Osteoarthritis in the neck 25 and spine 26 is often debilitating and may result in the patient being bed-ridden. To treat the diseased sites of osteoarthritis, the gel can be administered locally at the target sites discussed above utilizing a cannula or needle that penetrates beneath the skin to the target site.

In various embodiments, the gel is used to treat or manage pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

The term "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

Figure 4:
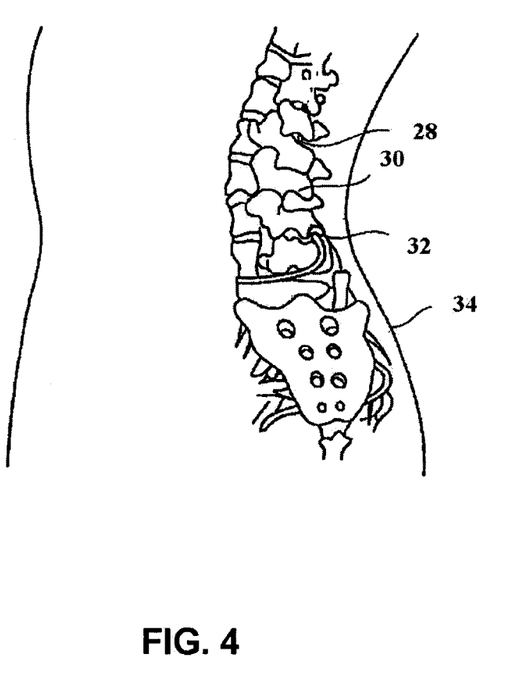
FIG. 4 illustrates a schematic dorsal view of the spine and sites where the pharmaceutical gel can locally be administered thereto.

One exemplary embodiment where the gel is suitable for use in pain management (e.g., neuropathic pain management) and/or to treat conditions (e.g., sciatica) is illustrated in FIG. 4. Schematically shown in FIG. 4 is a dorsal view of the spine and sites where the gel containing the drug depot or the drug depot held in position by the gel may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, the gel allows accurate placement of the drug depot in a manner to optimize location, accurate spacing, and drug distribution.

Although the spinal site is shown, as described above, the gel can be used to deliver a drug depot to any site beneath the skin, including, but not limited to, at least one muscle, ligament, tendon, cartilage, synovial joint, spinal disc, spinal foraminal space, near the spinal nerve root, facet joint, or spinal canal.

In various embodiments, the gel may have the therapeutic agent suspended therein and deployed around a targeted tissue site (e.g., a nerve root). The gel, either viscous or solid once deployed, keeps the therapeutic agent closely bound to target site (e.g., a nerve root) providing a therapeutically effective dosage of the therapeutic agent to the target site, with the dosage gradient rapidly falling off outside of the region of the gel. The therapeutic agent is therefore tightly targeted to the desired tissue site.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A gel for delivering a therapeutic agent to a target tissue site beneath the skin of a patient, the gel being capable of adhering to the target tissue site and comprising one or more biodegradable depots containing an effective amount of the therapeutic agent, the therapeutic agent comprising clonidine, wherein the target tissue site comprises at least one muscle, ligament, tendon, cartilage, spinal disc, spinal foraminal space near the spinal nerve root, facet or synovial joint, or spinal canal, and the gel has a pre-dosed modulus of elasticity in the range of about $1 \times 10^4$ to about $3 \times 10^5$ dynes/cm$^2$, and a post-dosed modulus of elasticity in the range of $1 \times 10^5$ to about $7 \times 10^5$ dynes/cm$^2$.

2. A gel for delivering a therapeutic agent according to claim 1, wherein the gel is sprayable and hardens after contacting the target tissue site.

3. A gel for delivering a therapeutic agent according to claim 1, wherein the therapeutic agent is encapsulated in a plurality of depots comprising microparticles, microspheres, microcapsules, and/or microfibers suspended in the gel.

4. A gel for delivering a therapeutic agent according to claim 3, wherein the gel further comprises a bolus dose of the therapeutic agent suspended in the gel to provide an immediate release of the therapeutic agent and the effective amount of the therapeutic agent is encapsulated in the plurality of microparticles, microspheres, microcapsules, microfibers, and/or depot particles to provide sustained release of the therapeutic agent over time.

5. A gel for delivering a therapeutic agent according to claim 1, wherein the gel comprises polyethylene glycol.

6. A gel for delivering a therapeutic agent according to claim 1, wherein the gel comprises a hydrogel.

7. A gel for delivering a therapeutic agent according to claim 1, wherein the gel comprises a radiographic marker adapted to assist in radiographic imaging.

8. A gel for delivering a therapeutic agent according to claim 7, wherein the radiographic marker comprises barium, calcium, and/or metal beads.

* * * * *

UNITED STATES PATENT AND TRADEMARK OFFICE
CERTIFICATE OF CORRECTION

PATENT NO. : 9,861,697 B2
APPLICATION NO. : 15/144129
DATED : January 9, 2018
INVENTOR(S) : Zanella et al.

Page 1 of 1

It is certified that error appears in the above-identified patent and that said Letters Patent is hereby corrected as shown below:

In the Specification

Column 1, Line 9, delete "SKIN"," and insert -- SKIN", now Pat. No. 9,327,030, --, therefor.

Column 4, Line 62, delete "a the" and insert -- the --, therefor.

Column 6, Line 20, delete "TNF-α," and insert -- TNF-α), --, therefor.

Column 6, Lines 40-42, delete "[2-hydroxy-5-[-4-[C2-pyridinylamino)sulfonyl]azo]benzoic acid]," and insert -- [2-hydroxy-5-[-4-(C2-pyridinylamino)sulfonyl]azo]benzoic acid], --, therefor.

Column 7, Line 29, delete "then" and insert -- than --, therefor.

Column 8, Line 19, delete "polyglycolide (PG)," and insert -- polyglycolide (PGA), --, therefor.

Column 10, Line 22, delete "polyglycolide (PG)," and insert -- polyglycolide (PGA), --, therefor.

Signed and Sealed this
Twenty-sixth Day of June, 2018

Andrei Iancu
*Director of the United States Patent and Trademark Office*